(12) United States Patent
Auriol et al.

(10) Patent No.: US 12,290,587 B2
(45) Date of Patent: May 6, 2025

(54) ANTI-AGING COSMETIC COMPOSITIONS

(71) Applicant: GIVAUDAN SA, Vernier (CH)

(72) Inventors: Daniel Auriol, Rogues sur Garonne (FR); Romain Reynaud, Toulouse (FR); Amandine Scandolera, Reims (FR)

(73) Assignee: GIVAUDAN SA, Vernier (CH)

( * ) Notice: Subject to any disclaimer, the term of this patent is extended or adjusted under 35 U.S.C. 154(b) by 870 days.

(21) Appl. No.: 17/437,954

(22) PCT Filed: Mar. 30, 2020

(86) PCT No.: PCT/EP2020/058900
§ 371 (c)(1),
(2) Date: Sep. 10, 2021

(87) PCT Pub. No.: WO2020/201185
PCT Pub. Date: Oct. 8, 2020

(65) Prior Publication Data
US 2022/0160607 A1    May 26, 2022

(30) Foreign Application Priority Data
Mar. 29, 2019 (GB) .................................... 1904469

(51) Int. Cl.
*A61K 8/24* (2006.01)
*A61K 8/34* (2006.01)
*A61K 8/60* (2006.01)
*A61Q 19/08* (2006.01)

(52) U.S. Cl.
CPC ................ *A61K 8/602* (2013.01); *A61K 8/24* (2013.01); *A61K 8/345* (2013.01); *A61K 8/60* (2013.01); *A61Q 19/08* (2013.01)

(58) Field of Classification Search
None
See application file for complete search history.

(56) References Cited

U.S. PATENT DOCUMENTS

| | | |
|---|---|---|
| 2003/0031689 A1 | 2/2003 | Mammone |
| 2010/0190727 A1 | 7/2010 | Simonnet et al. |
| 2012/0071425 A1 | 3/2012 | Ferguson et al. |

FOREIGN PATENT DOCUMENTS

| | | | |
|---|---|---|---|
| DE | 19503423 A1 | | 8/1996 |
| DE | 10143080 A1 | | 3/2003 |
| EP | 1421853 A1 | | 5/2004 |
| EP | 1835812 B1 | | 9/2007 |
| EP | 2204162 A1 | | 7/2010 |
| ES | 2370123 T3 | | 12/2011 |
| WO | 9623479 A1 | | 8/1996 |
| WO | WO1996023479 | * | 8/1996 |
| WO | 9806406 A1 | | 2/1998 |
| WO | 2007105071 A2 | | 9/2007 |

OTHER PUBLICATIONS

International Search Report and Written Opinion of the International Searching Authority for corresponding application PCT/EP2020/058900 dated Jul. 8, 2020.

\* cited by examiner

*Primary Examiner* — Traviss C McIntosh, III
(74) *Attorney, Agent, or Firm* — Norris McLaughlin PA

(57) ABSTRACT

A cosmetic active agent comprising a mixture of mannose-6-phosphate and mannose is disclosed.

16 Claims, 4 Drawing Sheets

ANTI-AGING COSMETIC COMPOSITIONS

Figure 1:
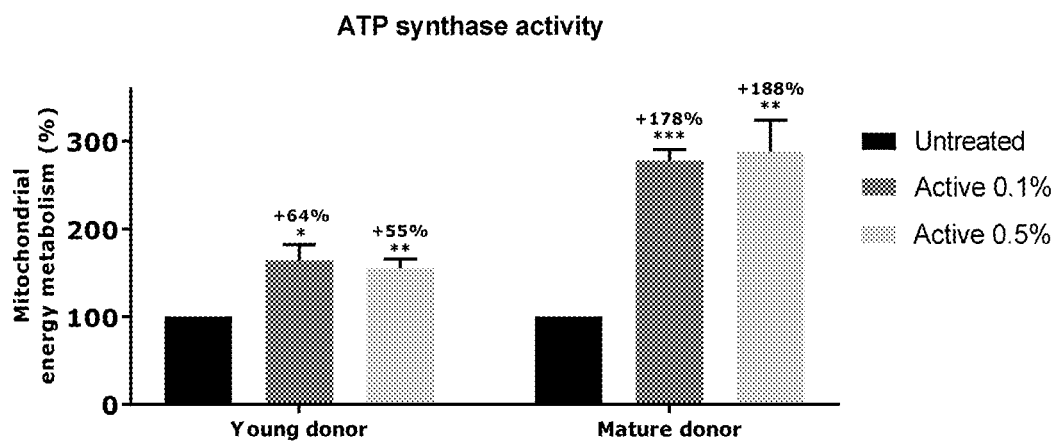

This is an application filed under 35 USC 371 based on PCT/EP2020/058900 (WO 2020/201185), filed 30. Mar. 2020, which in turn is based on GB 1904469.2 filed 29. Mar. 2019. The present application claims the full priority benefit of these prior applications and herein incorporates by reference the full disclosures of these prior applications.

The invention relates to active ingredients and methods that are useful to reduce the visible signs of aging on human skin. More specifically, the invention relates to a cosmetic active agent comprising a mixture of mannose-6-phosphate and mannose, and to its use for reducing wrinkles and age spots, as well as for structuring collagen fibers.

The desire to appear attractive is naturally rooted in modern consumers. Even as the ideal of attractiveness undergoes change over the course of time, it is universally accepted that the condition and appearance of our skin is a significant contributor to an attractive outward appearance.

Today's consumers are offered a multitude of cosmetic products for the care of skin. Generally, these products are in the form of creams and lotions, containing water for moisturizing the skin, and fats and lipids for re-greasing it, and their effects are exerted on the outer-most layer of the skin.

The provision of effective cosmetic preparations useful in the treatment of the causes of skin-aging and thereby reducing the visible signs of aging remains an unmet need.

The structural framework of the skin is referred to as its extracellular matrix. This internal framework comprises a network of inter-meshed polymers, such as collagen and elastin, inside which skin cells are contained. It is responsible for the skin's mechanical properties, including firmness, strength, suppleness and elasticity. The physical signs of skin aging are a reflection of the condition of the skin matrix. More particularly, the weaker and less regular the matrix, the more wrinkles, roughness and sag the skin tends to have.

The reticular dermis is the lower layer of the dermis, found under the papillary dermis, composed of dense irregular connective tissues and featuring densely packed collagen fibers. These protein fibers give the dermis its properties of strength, extensibility, and elasticity. The orientation of collagen fibers within the reticular dermis creates lines of tension called Langer's lines, which are essential for wound healing and mechanical properties.

Mitochondria are unique organelles which are the power generators of cells, converting oxygen and nutrients into adenosine triphosphate (ATP), the chemical energy that allows cell metabolism. Mitochondria are able to synthesize proteins independently from the cell nucleus and cytoplasm. They represent an important factor in human evolution by supporting essential cell functions (energy powerhouse, protection of DNA, signaling of cell reproduction, activation of cell apoptosis, maintenance of cell electrochemical integrity . . . ).

A decline in mitochondrial activity has been associated with normal cell aging. With age and external stresses, some damages are done to the mitochondria of dermal fibroblasts, leading to Reactive Oxygen Species (ROS) production and inadequate energy production in the process to convert oxygen into energy. As a consequence, the genes expression pattern of dermal fibroblasts will be changed, causing a disturbance in collagen production, inflammation, disruption of detoxification pathway (proteasome) and oxidation of skin pigments (lipofuscin), leading to disorganization of the extracellular matrix (ECM), premature skin aging and apparition of age spots.

A change in the production pattern of collagen in the ECM, caused by any of the phenomena described before, will lead to a disorganization of the reticular dermis, changes in packing of the fibers and a decline of mechanical properties in the skin. The complex hierarchical structure of collagen can be evaluated using Atomic Force Microscopy (AFM). This technique scans the surface of skin cells or skin sections, using a sharp tip which will identify and follow the relief of the support during the scanning. This method therefore gives information about biomechanical properties and topography of the studied skin.

There remains a need to provide methods and cosmetic active agents for application to the skin that can efficiently reverse or reduce undesired signs of skin aging, such as age spots or wrinkles.

It has been known from prior art that mannose-6-phospate can have a positive effect on skin appearance. For example, US 2012/0071425 A1 describes improvements of the macroscopic properties of the skin using mannose-6-phosphate, such as reducing redness of skin.

Further, it is known that monosaccharides, such as mannose or rhamnose, may reduce the signs of aging of the skin (US 2010/0190727 A1).

However, the inventors of the present invention have surprisingly found that a mixture of mannose-6-phosphate and mannose in a specific molar ratio shows an enhanced effect on the reduction of the signs of skin aging.

The present invention provides a cosmetic active agent comprising a mixture of mannose-6-phosphate and mannose, wherein the molar ratio of mannose-6-phosphate to mannose is from 3:1 to 0.3:1.

Within this application, this mixture of mannose-6-phosphate and mannose at the specified ration is sometimes also called "mannose-6-phosphate complex". Therefore, this term is meant to have the same meaning as "the cosmetic active agent of the present invention" or "the mixture of mannose-6-phosphate and mannose" or other similar terms.

The cosmetic active agent of the present invention is able to significantly reduce the signs of skin aging, such as wrinkles and age spots.

The cosmetic active agent of the present invention may comprise D-mannose-6-phosphate, L-mannose-6-phosphate, or a mixture thereof. Preferably, it comprises D-mannose-6-phosphate.

Likewise, the cosmetic active agent of the present invention may comprise D-mannose, L-mannose, or a mixture thereof. Preferably, it comprises D-mannose.

Throughout this application, if not specified differently, the terms "mannose-6-phosphate" and "mannose" are meant to encompass both the D- and L-forms, as well as mixtures thereof.

In the cosmetic active agent of the present invention, mannose-6-phosphate may be present in any cosmetically acceptable form. For instance, depending on the pH, mannose-6-phosphate may be present in protonated form or in the form of a salt. Suitable counterions include, but are not limited to, monovalent cations, such as e.g. sodium, potassium, or ammonium; divalent cations, such as e.g. copper, zinc, calcium, magnesium, or manganese; or trivalent cations, such as e.g. aluminum; or mixtures thereof. Mannose-6-phosphate may also be mixed with one or more amino acids, e.g. lysine or arginine, and/or with any other cosmetically acceptable positively charged substance(s), and may form a salt with said amino acid(s) and/or other cosmetically acceptable positively charged substance(s). Preferably, mannose-6-phosphate is present as a sodium or lysine or arginine salt or as a salt of a divalent cation.

Throughout this application, if not specified differently, the term "mannose-6-phosphate" is meant to encompass both the protonated form and any cosmetically acceptable salt of mannose-6-phosphate, as well as mixtures thereof.

Preferably, the molar ratio of mannose-6-phosphate to mannose is from 2:1 to 1:1, more preferably from 1.9:1 to 1.1:1, in particular about 1.5:1.

The mixture of mannose-6-phosphate and mannose may be used in pure form or in combination with other active ingredients and/or excipients.

Therefore, in one embodiment, the cosmetic active agent at least essentially consists of the mixture of mannose-6-phosphate and mannose.

Preferably, the cosmetic active agent of the present invention comprises mannose-6-phosphate in a concentration of 30 to 220 mM, more preferably in a concentration of 60 to 170 mM, and most preferably in a concentration of about 120 mM.

In particular, the cosmetic active agent of the present invention may comprise from 0.5 to 6.0 wt % of mannose-6-phosphate sodium salt, more preferably from 2.0 to 4.0 wt % of mannose-6-phosphate sodium salt, and most preferably about 3.0 wt % of mannose-6-phosphate sodium salt. Alternatively, the cosmetic active agent of the present invention may comprise mannose-6-phosphate in any other form described above, in corresponding amounts.

Preferably, the cosmetic active agent of the present invention comprises from 0.5 to 5.0 wt % of mannose, more preferably from 0.8 to 3.0 wt % of mannose, and most preferably about 1.5 wt % of mannose.

In an embodiment, the cosmetic active agent of the present invention further comprises glycerol and/or sodium phosphate.

Alternatively or in addition, the cosmetic active agent of the present invention may further comprise 1,2-propanediol and/or water. In particular, glycerol may be replaced by 1,2-propanediol at a concentration of up to 30% or by water.

In a preferred embodiment, the cosmetic active agent of the present invention further comprises:

| | |
|---|---|
| 2.0 to 4.0 wt % | mannose-6-phosphate sodium salt |
| 0.8 to 3.0 wt % | mannose |
| up to 0.2 wt % | sodium phosphate |
| 50 wt % | glycerol |
| qsp 100 wt % | water |

The cosmetic active agent of the present invention may be at any pH suitable for cosmetic application, e.g. at a pH of 1.5 to 9.0, more preferably at a pH of 3.0 to 6.5, and most preferably at a pH of 4.5 to 6.0, e.g. ata pH of about 5.

The cosmetic agent of the present invention is advantageously used in cosmetic compositions, in particular in skin care compositions.

Therefore, in a further aspect, the present invention provides a cosmetic composition, and in particular a skin care composition, comprising the above described cosmetic active agent and a cosmetically acceptable excipient.

More particularly, the present invention provides an anti-aging skin care composition.

In a further aspect, the present invention provides a method of reducing the signs of aging in skin, comprising the step of applying the cosmetic active agent of the present invention or the cosmetic composition of the present invention to the skin, in particular to facial skin.

It has been found that by applying the cosmetic active agent of the present invention or the cosmetic composition of the present invention to the skin, it is possible to reduce wrinkles.

It has further been found that by applying the cosmetic active agent of the present invention or the cosmetic composition of the present invention to the skin, it is possible to reduce age spots.

It has still further been found that by applying the cosmetic active agent of the present invention or the cosmetic composition of the present invention to the skin, it is possible to structure collagen fibers.

The cosmetic active agent of the present invention is able to:

reprogram mitochondrial energy metabolism in older cells,
promote skin matrix restructuring,
reinforce the dermo epithelial junction (DEJ),
reorganize the skin matrix similar to that of younger skin,
significantly reduce visible age spots,
visibly reduce crow's feet wrinkles, and
reduce neck wrinkles to remodel the Y-shape of the face.

These effects have been confirmed by in vitro, ex vivo and clinical studies as described in the examples below.

In particular, the cosmetic active agent of the present invention was found to increase ATP synthase activity and citrate synthase activity, correlating to a reactivation of cell metabolism and mitochondrial biogenesis (example 3).

At the same time, the cosmetic active agent of the present invention does not promote protein glycation, which is involved in age-related disorders (example 4).

The cosmetic active agent of the present invention was further found to stimulate genes controlling extracellular matrix component, matrix cohesion and fibroblasts multiplication (example 5). This leads to an improvement of the dermis restructuration.

Treatment with the cosmetic active agent of the present invention also leads to an increase in type V Collagen, Fibulin-1 and Tenascin-C expression (example 6). These results evidence a significant improvement of the dermis structure and organization.

These results were confirmed by ex vivo studies, which evidenced a strong impact of the cosmetic active agent of the present invention on the dermis and its organization and restructuration (example 7).

Collagen fibers in the dermis of a young person are typically very cohesive, well-organized and parallel, whereas a mature skin typically displays a much coarser and disorganized collagen fiber network. Treating mature skin with the cosmetic active agent of the present invention led to a significantly improved collagen fiber organization and increased cohesion between them (example 8).

Proteins in skin are modified through oxidation, glycation and carbamylation. These modified proteins are continuously eliminated by proteasome activity. However, upon skin aging, the proteasome activity is slowed down, resulting in an accumulation of modified proteins. As a consequence, various skin disorders can appear, such pigment spots, age spots, and invisible spots. It has now been found that the cosmetic active agent of the present invention is able to stimulate proteasome activity (example 9).

UV irradiation increases the amount of oxidized proteins in epidermis and dermis. Interestingly, the cosmetic active agent of the present invention not only prevents this increase, but even significantly reduces the amount of oxidized proteins (example 10).

Further in vitro comparison of the mixture of mannose-6-phosphate and mannose (also called "mannose-6-phosphate complex") according to the present invention, mannose and mannose-6-phosphate regarding their effect on mitochondrial mass reduction showed a significantly lower effect on mitochondrial mass reduction than the mixture, indicating a synergistic biological effect of the mixture on reducing the signs of cell aging (example 11).

Clinical studies confirmed that the cosmetic active agent of the present invention is able to significantly reduce the number and size of visible spots (example 13).

Furthermore, the cosmetic active agent of the present invention significantly improves collagen density and organization (example 13).

The cosmetic active agent of the present invention also causes a significant reduction of crow's feet wrinkles (example 13).

Last but not least, the cosmetic active agent of the present invention is able to significantly reduce neck wrinkles, both in terms of volume and depth (example 14).

Particular uses of the cosmetic active agent of the present invention include, but are not limited to, anti-aging serums or creams, anti-aging products for the reduction of deep wrinkles, intensive treatments for facial rejuvenation, nasolabial anti-wrinkles products, anti teck-neck products, anti-crows' feet products, anti-age spots serums, skincare for mature skin, and dermocosmetics.

Mannose-6-phosphate (M6P) is a human metabolite used to generate energy the cells and to drive proper functions. It is an essential component to promote glycolysis in the cell (fostering energy production).

The cosmetic active agent of the present invention can be prepared from a vegetal source using green chemistry.

Mannose-6-phosphate may be prepared from mannose by an enzymatic phosphorylation. Suitable phosphorylation conditions are described, for instance, in WO 2008/142155 A2, the contents of which in this respect are herewith incorporated by reference. Example 1 below describes a possible synthesis of mannose-6-phosphate in detail.

The enzymatic phosphorylation typically provides a mixture of mannose-6-phosphate and mannose. Depending on the reaction time and other conditions, the conversion and thus the ratio of mannose-6-phosphate to mannose may vary. Thus, preferably, the reaction time and conditions are chosen such that the desired mannose-6-phosphate to mannose ratio is obtained directly. Alternatively, it is also possible to adjust the ratio by adding or removing one or both of the products.

Preferably, the cosmetic active agent of the present invention comprises from 0.5 to 5.0 wt % of mannose, more preferably from 0.8 to 3.0 wt % of mannose, and most preferably about 1.5 wt % of mannose.

The molar ratio of mannose-6-phosphate to mannose in the cosmetic active agent of the present invention is from 3:1 to 0.3:1, more preferably from 2:1 to 1:1, most preferably from 1.9:1 to 1.1:1, and in particular about 1.5:1.

The concentration of mannose-6-phosphate in the cosmetic active agent of the present invention is preferably from 30 to 220 mM, more preferably from 60 to 170 mM, and most preferably about 120 mM.

The concentration of mannose in the cosmetic active agent of the present invention is preferably from 0.5 to 5.0 wt %, more preferably from 0.8 to 3.0 wt %, and most preferably about 1.5 wt %.

The above ratios and concentrations have been found to provide optimal anti-aging activity to the skin.

The cosmetic active agent of the present invention may optionally further contain other cosmetically active ingredients. Any cosmetically active ingredients commonly used in the preparation of cosmetic preparations for use on the human skin may be employed in the present invention.

The cosmetic active agent of the present invention may optionally further contain solvents, excipients, and/or other adjuvants. Any solvents, excipients, and/or other adjuvants commonly used in the preparation of cosmetic preparations for use on the human skin may be employed in the present invention.

In particular, the cosmetic active agent of the present invention may further comprise glycerol. Glycerol may serve as a preservative.

Alternatively or in addition, the cosmetic active agent of the present invention may further comprise sodium phosphate. Sodium phosphate may be used as a buffer, for instance.

In a second aspect, the present invention provides a cosmetic composition comprising the cosmetic active agent of the present invention, in particular in the preferred embodiments outlined herein.

Typically, the cosmetic active agent of the present invention will be used in a concentration of about 0.1 to 5.0 wt % in the cosmetic composition, more preferably in a concentration of about 0.5 to 5.0 wt %, for instance in a concentration of about 3 wt %.

More particularly, the present invention provides a skin care composition, especially an anti-aging skin care composition.

The cosmetic composition of the present invention typically further comprises a cosmetically acceptable excipient.

Cosmetic compositions, and in particular skin care compositions, of the present invention may contain one or more cosmetically acceptable excipients. Any excipients commonly used in the preparation of cosmetic preparations for use on the human skin may be employed in the present invention. Suitable excipients include, but are not limited to ingredients that can influence organoleptic properties, penetration of the skin, and the bioavailability of the cosmetic active agent of the present invention. More specifically, they include liquids, such as water, oils or surfactants, including those of petroleum, animal, plant or synthetic origin, such as and not restricted to, peanut oil, soybean oil, mineral oil, sesame oil, castor oil, polysorbates, sorbitan esters, ether sulfates, sulfates, betaines, glycosides, maltosides, fatty alcohols, nonoxynols, poloxamers, polyoxyethylenes, polyethylene glycols, dextrose, glycerol, digitonin, and the like.

The formulation for topical application to the skin may take any physical form. For instance, the cosmetic composition, and in particular the skin care composition, may be in the form of a liposome composition, mixed liposomes, oleosomes, niosomes, ethosomes, milliparticles, microparticles, nanoparticles and solid-lipid nanoparticles, vesicles, micelles, mixed micelles of surfactants, surfactant-phospholipid mixed micelles, millispheres, microspheres and nanospheres, liposphere, millicapsules, microcapsules and nanocapsules, as well as microemulsions and nanoemulsions, which can be added to achieve a greater penetration of the cosmetic active agent of the present invention.

The cosmetic composition, and in particular the skin care composition, may be produced in any solid, liquid, or semi-solid form useful for application to the skin topically or by transdermal application. Thus, these preparations of topical or transdermal application include, but are not restricted to, creams, multiple emulsions, such as and not restricted to, oil and/or silicone in water emulsions, water-in-oil and/or silicone emulsions, water/oil/water or water/silicone/water type emulsions, and oil/water/oil or silicone/water/silicone type emulsions, micro-emulsions, emulsions and/or solutions, liquid crystals, anhydrous compositions, aqueous dispersions, oils, milks, balsams, foams, aqueous or oily lotions, aqueous or oily gels, cream, hydro-alcoholic solutions, hydro-glycolic solutions, hydrogels, liniments, sera, soaps, face masks, serums, polysaccharide films, ointments, mousses, pomades, pastes, powders, bars, pencils and sprays or aerosols (sprays), including leave-on and rinse-off formulations.

In order to achieve the beneficial effects described herein, the cosmetic active agent or cosmetic composition of the present invention are advantageously applied to the skin, in particular to facial skin.

Throughout this application, the term "skin" refers in particular to human skin.

The present invention thus also provides a method of reducing the signs of aging in skin, comprising the step of applying the cosmetic active agent or the cosmetic composition of the present invention to the skin. In particular, the method comprises the application to facial skin.

The effects of the cosmetic active agent and cosmetic composition of the present invention are particularly advantageous for skin areas that are visible and exposed, and that commonly display signs of aging, such as wrinkles or age spots. These include, but are not limited to, the face, neck, neckline, hands and forearms.

The present invention also relates to the use of the cosmetic active agent or the cosmetic composition of the present invention for reducing the signs of aging in skin.

This use includes, in particular, the reduction of wrinkles, the reduction of age spots, and/or the structuring of collagen fibers.

The present invention is further illustrated by means of the following non-limiting examples:

EXAMPLE 1

Preparation of D-Mannose-6-Phosphate

General

Mannose-6-phosphate was obtained by reacting between mannose with condensed phosphoric acid, in particular pyrophosphate, and in the presence of the acid phosphatase from *Shigella flexneri*. Mannose-6-phosphate was then purified by removing the excess of condensed phosphoric acid and the released phosphate, optionally followed by removing residual mannose.

Acid Phosphatase from *Shigella flexneri*

The gene from the acid phosphatase from *Shigella flexneri* (usual name PhoN-Sf) was ordered and synthesized by DNA 2.0, now ATUM (Newark, CA, USA) (UniProt accession number O50542). The gene was cloned into pET-26b (+) and the expression vector was subsequently transformed into *E. coli* BL21 (DE3) cells.

PhoN-Sf was expressed using autoinduction medium (B. G. Fox and P. G. Blommel, Curr Protoc Protein Sci 2009, doi:10.1002/à471140864.ps0523s56; reference 71491, Novagen, Merck KGaA, Darmstadt, Germany). Cells were collected by centrifugation and the supernatant was discarded. The PhoN-Sf enzyme was isolated as follows: cells were lysed using PandaPlus 2000 homogenizer (GEA Niro Soavi, Parma, Italy), cell debris was removed by centrifugation and ultrafiltration (GE Healthcare, MW cut off 750 kDa), and the enzyme contained in the filtrate was used as is or after concentration (vacuum evaporation at 30° C.).

PhoN-Sf enzyme activity was assayed spectrophotometrically by measuring the dephosphorylation of 4-nitrophenylphosphate (p-NPP) via release of p-nitrophenol. The reaction medium contained 104 mM sodium citrate buffer pH 4.80, 5.8 mM magnesium chloride, 0.11 mM zinc chloride, 1.15 mM p-NPP, properly diluted enzyme (activity ranging from 0.1 to 0.8 U/mL). The mixture was incubated at 30° C. and at regular time intervals, 100 µL of reaction medium was mixed with 200 µL of 0.5 N NaOH (reaction quenching). A volume of 250 µL was then introduced into a well of a 96-wells microplate and the absorbance was measured at 405 nm.

One unit of phosphatase activity (U) corresponds to the amount of enzyme that releases one micromole of p-NP per minute under assay conditions.

Mannose-6-Phosphate Synthesis

The enzymatic reaction was carried out as follows:

D-Mannose, 0.15 or 0.225 M, disodium pyrophosphate, pH 4.15: 0.33 or 0.50 M, respectively, PhoN-Sf enzyme: 0.20 U/mL, magnesium and zinc chloride salts: 0.50 and 0.1 mM, respectively, temperature: 30° C.; moderate agitation, duration: 22 and 28 hours respectively.

Purification and Quantification

When it was decided to stop the reaction, the pH of the reaction medium was adjusted to 2.0 with a conveniently chosen acid. Residual disodium pyrophosphate and released phosphate were removed by sequential addition of magnesium and ammonium salts to reach a pH close to 9.5. The formed precipitate containing pyrophosphate, phosphate, magnesium and ammonium was removed by filtration. Magnesium and ammonium were removed using a cation exchange resin, and finally the pH of the solution was adjusted using concentrated sodium hydroxide to obtain D-mannose-6-phosphate sodium salt at a pH value ranging from 4.0 to 7.0.

The content of D-mannose-6-phosphate and D-mannose was measured using the K-MANGL enzymatic kit from Libios (Pontcharra sur Turdine, France). The complete kit indicates the amount of D-mannose-6-phosphate and D-mannose, whereas a modified kit, in which ATP is removed, allows measuring the concentration of D-mannose-6-phosphate only; the difference between both values gives the concentration of D-mannose.

The above process provides a mixture of D-mannose-6-phosphate and D-mannose in a molar ratio of about 1.5:1.

Optionally, D-mannose and D-mannose-6-phosphate can be separated using an anion ex-change resin.

The cosmetic active agent used for the studies described below contained 105.05 mmol/kg of D-mannose-6-phosphate sodium salt and 87.42 mmol/kg of D-mannose. It had a pH of 4.78.

EXAMPLE 2

Skin Care Composition Comprising Mannose-6-Phosphate

For the clinical studies described below (examples 12 and 13), the following composition was prepared:

| Ingredient (INCI Name) | Quantity (wt %) |
|---|---|
| AQUA/WATER | 85.70 |
| CETYL ALCOHOL, GLYCERYL STEARATE, PEG-75 STEARATE, CETETH-20, STEARETH-20 | 5.0 |
| ISODECYL NEOPENTANOATE | 4.5 |
| SODIUM MANNOSE-6-PHOSPHATE, GLYCEROL | 4.0 |
| PHENOXYETHANOL, METHYL PARABEN, PROPYL PARABEN, ETHYL PARABEN | 0.4 |
| DIMETHICONE | 0.3 |
| FRAGRANCE, LINALOOL, D-LIMONENE | 0.1 |

This corresponds to test composition 2 mentioned in example 4.

EXAMPLE 3

Mitochondrial Energy Metabolism

Cellular Model

Normal Human Epidermal Keratinocytes NHEK (adult single donor, ref C-12003, PromoCell) were cultured in Keratinocyte Growth Medium 2 (PromoCell, ref C-20011) according to the manufacturer's recommendations.

Lot 415Z005.2 (breast, single donor, female, Caucasian, 26 years old)=>"Young"

Lot 409Z012.1 (breast, single donor, female, Caucasian, 51 years old)=>"Mature"

Tested Compound and Treatment

Test composition 1 was prepared by diluting the mixture of D-mannose-6-phosphate and D-mannose obtained according to example 1 at 0.5% and 0.1% (v/v) in Keratinocytes Growth Medium 2 (KGM2; a culture medium).

The cells were treated the day after seeding and incubated for 72 h with the test composition 1 at 0.1% or 0.5%. Untreated condition, i.e. incubation for 72 h without the active, was used a basal reference. It was noticed that at early cell passages, the young donor cells grew more rapidly than the mature donor cells.

ATP Synthase Activity

The cells were seeded in 6-well plates at 150'000 cells/well (young donor) or 180'000 cells/well (mature donor). After treatment, the cells were harvested by trypsination, counted on Kova slide and kept at 4° C. until measurements. For each run, 400'000 cells were permeabilized and incubated in Tris buffer (pH 8) with 0.5 mM ATP, 0.5 mM NADH, 9 UI PK/LDH (pyruvate kinase/lactate dehydrogenase), 2 mM PEP (phosphoenolpyruvate) and 10 µM antimycin A in 96-well plates. The activity was measured in real-time by spectrofluorimeter (Tecan Infinite 200; DO at 340 nm). Results are expressed in percent of ATP synthase activity after normalization on untreated cells (100% activity) and oligomycin A (1 µM; 0% activity).

Citrate Synthase Activity

The cells were seeded in 24-well plates at 40'000 cells/well. After treatment, the cells were harvested by trypsination, counted on Kova slide and kept at 4° C. until measurements. Then 30'000 cells were permeabilized and incubated in 10 mM Tris (pH 8) with 150 µM 5,5'-Dithio-bis 2-nitrobenzoic acid, 300 µM acetylCoA and 1 mM oxaloacetate in 96-well half area microplates. The enzymatic activity was measured in real-time by spectrofluorimeter (Tecan Infinite 200; DO at 415 nm). Results are expressed in percent of citrate synthase activity after normalization on untreated cells (100% activity).

Calculations

Calculations were done first on each simplicate and the mean was calculated on the percentage of inhibition in each simplicate.

Effective concentration 50 and 20: calculations were done with each triplicate by using a non-linear regression in Graphpad Prism4. The EC50s and EC20s were calculated in reference to positive and negative controls.

Percentage of ATP Synthase Activity:

$$\% \text{ activity} = 100 \times (\text{Slope}_{oligomycin} - \text{Slope}_{sample}) / (\text{Slope}_{oligomycin} - \text{Slope}_{untreated})$$

with Slope: slope of curve (variation of optical density in function of time)

Percentage of Citrate Synthase Activity:

$$\% \text{ activity} = 100 \times (\Delta OD_{background} - \Delta OD_{product}) / (\Delta OD_{background} - \Delta OD_{untreated})$$

with $\Delta OD$: variation of optical density in function of time

Results

Test composition 1 was found to significantly increase the ATP synthase activity after 72 h of incubation at 0.1% and 0.5% in each donor. The results are shown in FIG. 1. The efficacy was more pronounced in the mature donor, demonstrating the impact on the reactivation of cell metabolism in impaired condition. Indeed, the effect was 2.9 times more pronounced relative to untreated condition on mature donor.

Figure 2:
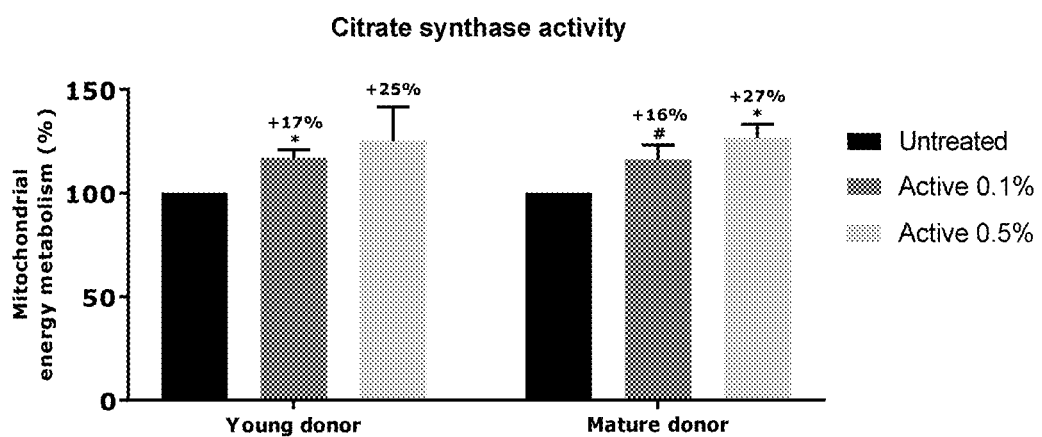

Test composition 1 was also found to increase the mitochondrial biogenesis via the citrate synthase. The results are shown in FIG. 2. The effect was equivalent in young and mature donor, showing an increase of citrate synthase activity after 72 h of incubation at 0.1% and 0.5%. These results evidence that the cosmetic active agent of the present invention is able to reactivate the mitochondrial biogenesis.

EXAMPLE 4

Advanced Glycation End Products (AGEs) Production

Treatment of Skin Explants

Skin explants from a 45 years old donor were stabilized with DMEM medium supplemented with antibiotics (penicillin 100 U/mL and streptomycin 100 µg/mL) and fetal calf serum 5% for 4 hours at 37° C./5% $CO_2$.

For example 4, test composition 2 was prepared by diluting the mixture of D-mannose-6-phosphate and D-mannose obtained according to example 1 at 4% (v/v) in emulsion. Test composition 2 corresponds to the cosmetic composition described in example 2.

The explants were treated for 48 hours with test composition 2. For comparison, explants were treated with a placebo composition containing everything but the mixture of D-mannose-6-phosphate and D-mannose. Three explants per condition (untreated at T0, treated with test composition 2 and treated with the placebo composition) were then frozen immediately in liquid nitrogen for preservation before cutting.

Immunostaining of AGEs

Frozen skin explants were included in Tissue-Tek® before being cut with the cryostat. The sections had a thickness of 10 µM. The slides were stored at −20° C. before being dried and then fixed with acetone.

Specific sites were blocked; primary antibody directed against AGEs was incubated at room temperature, as was the secondary antibody coupled with Alexa-type fluorochromes. The nuclei were labeled with DAPI (Roche), a fluorescent marker specific for DNA. After each incubation, the sections were washed 3 times.

Finally, the slides were mounted with a mounting medium and observed under a fluorescence microscope (Olympus CK40) with filters adapted to different fluorochromes. The images were made with the x40 lens.

Fluorescence Quantification

Fluorescence quantification was performed using ImageJ software. Fluorescence of the total area of the section was measured on all images without DAPI. Shapiro Wilk test was performed which allowed using student test to compare conditions.

Results

It was found that test composition 2 did not induce an increase of AGEs in the skin explant after 2 days of topical application. Consequently, protein glycation (which is involved in age-related disorders) is not promoted by cosmetic active agent of the present invention in skin explants.

EXAMPLE 5

Skin Matrix Restructuration: Transcriptomic Analysis

Normal Human Dermal Fibroblasts NHDFs from a 28 years old donor were seeded at 300'000 cells per well in a 6-wells plate in DMEM (Dulbecco's Modified Eagle's Medium) medium complemented with 10% of FCS (Fetal calf serum). After 48 h of culture, NHDFs were rinsed two times with PBS and allowed to rest in DMEM medium FCS-Free overnight before stimulation.

For example 5, test composition 3 was prepared by diluting the mixture of D-mannose-6-phosphate and D-mannose obtained according to example 1 at 4% (v/v) in DMEM culture medium (Dulbecco's Modified Eagle's Medium) complemented with 10% of FCS (Fetal calf serum).

Cells were stimulated with test composition 3 in DMEM medium FCS-free for 6 h. After 6 h of stimulation, total RNA was extracted by phenol-chloroform extraction. RNA quality was controlled and a reverse transcription was performed to obtain cDNA. RT-qPCR was made on specific plates designed to study transcriptomic expression of different genes involved in dermis biology for NHDFs with 10 ng of cDNA per well.

The results of gene expression obtained with fibroblasts were normalized according to POLR2A (RNA polymerase II, subunit A) and PES1 (pescadillo ribosomal biogenesis factor 1) housekeeping gene. The results were expressed following a data normalization with the untreated condition.

Results

The transcriptomic analysis was performed by RT-qPCR on dermis plates with 95 targeted genes involved in extracellular matrix, remodeling, antioxidant enzymes and stress defenses, neurotrophin pathway, cell proliferation, DNA repair and stem cell markers. The results are expressed in comparison with untreated condition used as a negative control and normalized with the average of the most stable housekeeping genes (POLR2A and PES1).

The results evidenced a very strong effect on dermal restructuration and remodeling through the up-regulation of CTGF, CYR61 and TGFB1. Indeed, these three genes encode proteins involved in regulation of tissue remodeling, regulation of collagen synthesis, and stimulation of fibroblasts proliferation.

More precisely, test composition 3 up-regulated RNA expression of different genes involved in extracellular matrix composition, such as CTGF (+80%*) and CYR61 (+84%*). CTGF, a connective tissue growth factor, is a regulator of collagen synthesis, and its up-regulation confirms the improvement of extracellular matrix structure. CYR61 (Cysteine-rich angiogenic inducer 61) encodes an extracellular matrix component, which helps and stimulates skin fibroblasts migration, encouraging dermis regeneration and restructuration.

The up-regulation of TGFB1 (Transforming growth factor beta 1) RNA expression (+18%**) evidences that dermis restructuration also happens thanks to an increase of fibroblasts proliferation.

In conclusion, the cosmetic active agent of the present invention showed a bioactivity at dermis level by stimulating genes controlling extracellular matrix component, matrix cohesion and fibroblasts multiplication. This leads to an improvement of the dermis restructuration.

EXAMPLE 6

Skin Matrix Restructuration: Immunohistochemistry Assay

NativeSkin® skin explant were used, a biopsy of human normal skin embedded in a solid and nourishing matrix. The epidermal surface was maintained in contact with air to allow topical application. The donor was a woman aged 59 years with Caucasian skin who had an abdominoplasty surgery.

For examples 6, 7, 8, and 9, test composition 4 was prepared by diluting the mixture of D-mannose-6-phosphate and D-mannose obtained according to example 1 at 4% (v/v) in PBS (Phosphate-buffered saline).

Test composition 4 was brought in contact with the NativeSkin® by topical application, which was removed and renewed every day during 7 days. The results were compared to the untreated skin explants.

Skin explants were fixed in formalin and embedded in paraffin. Biomarkers of interest—Type V Collagen, Fibulin-1 and Tenascin-C—were detected by immunofluorescence. The biomarkers' expressions were analyzed by fluorescence microscopy (DM5000B-Leica Microsystems); 10 images were acquired per biomarker.

The fluorescence was quantified for each picture by software imaging (Image J).

The region of interest was delimited and the total fluorescence intensity was calculated relative to the total area of interest. The values were compared to the control to express an activating or inhibiting effect. A statistical analysis was performed for each data with student test ($p<0.05$ *, $p<0.005$ and $p<0.0005$*).

Results

Type V Collagen is a fibrillary collagen. It is a minor component of the dermal matrix which associates with Collagen type I fibers. Type V Collagen expression was increased by +17% (p value<0.001) with test composition 4 at 4%.

Fibulin-1 is a component of the extracellular matrix. It is implicated in the dermo-epidermal junction (DEJ) but with a very low expression level. Test composition 4 increased the expression of Fibulin-1 by +13% (p value<0.01).

Tenascin-C is a matrix protein involved in the cell cohesion at the dermo-epidermal junction, and is located in the basal layers. Test composition 4 at 4% increased the expression of Tenascin-C by +51% (p value<0.001), allowing to preserve the cohesion of the dermo-epidermal junction.

These results strongly evidence that the cosmetic active agent of the present invention significantly improves the dermis organization through the over-expression of key proteins playing a role in the dermis structure and organization.

EXAMPLE 7

Skin Matrix Restructuration: Ex Vivo Morphological Analysis

For examples 6, 7, 8, and 9, test composition 4 was prepared by diluting the mixture of D-mannose-6-phosphate and D-mannose obtained according to example 1 at 4% (v/v) in PBS (Phosphate-buffered saline).

Immunohistochemistry assay was performed on a skin explant from the same donor of 59 years used for the immunohistochemistry staining, treated in the same conditions as described in example 6.

5 μm sections were performed. Obtained slices were stained with a Masson's Trichrome staining. Masson's Trichrome staining allows detection of collagen fibers and muscular tissue in histological slices.

Hematoxyline stains nucleus in purple, and fuchsine ponceau stains muscular fibers, erythrocytes, cytoplasm and elastic fibers in pink; Vert Lumière stains specifically collagen fibers.

Staining analysis was realized with LEICA® DFC 280 and several pictures representative of the slices were taken.

Immunostaining pictures were qualitatively analyzed to describe the state of the different skin compartments.
Results It was found that the skin explant treated with test composition 4 showed a similar epidermal morphology to the untreated control.

At the dermis level, the papillary dermis showed a morphology identical to the control sample, both for collagen fibers and elastic fibers, while the reticular dermis evidenced an increase of density with test composition 4 in comparison to the untreated condition.

These observations show that the cosmetic active agent of the present invention has a strong impact on the dermis and its organization and restructuration: The density of the reticular dermis is increased by 36%, the dermo-epidermal junction is better defined and the epidermis is more cohesive.

EXAMPLE 8

Skin Matrix Restructuration: Collagen Fibers Organization (AFM and SAXS Analyses)

Human skin explants of an average diameter of 12 mm (±1 mm) were prepared on each abdominoplasty coming from two different donors:
Young donor: a 30-year-old Caucasian woman
Mature donor: a 65-year-old Caucasian woman
The explants were kept in survival in BEM culture medium (BIO-EC's Explants Medium) at 37° C. in a humid, 5%-$CO_2$ atmosphere.

For examples 6, 7, 8, and 9, test composition 4 was prepared by diluting the mixture of D-mannose-6-phosphate and D-mannose obtained according to example 1 at 4% (v/v) in PBS (Phosphate-buffered saline).

Test composition 4 was applied topically on the basis of 2 μl per explant (2 mg/$cm^2$), and spread using a small spatula.

For the mature donor, test composition 4 was applied on D0, D1, D2, D3, D5, D6 and D7.

For comparison, control explants from both the young and the old donor were cultured for 8 days without special treatment expect for the renewal of the culture medium.

The culture medium was half renewed (1 mL) on D1, D4 and D6 for the young donor and on D2, D3 and D6 for the mature donor.

On D0, the explant from the batch T0 was collected and frozen at −80° C.

On D8, one explant of all batches was collected and treated the same way as T0.

The frozen samples were cut into 20-μm-thick sections using a Leica CM 3050 cryostat and then mounted on coverslips provided by Novitom, put on Superfrost® plus silanized glass slides.

The samples were cryofixed after treatment. 20 μm thick cold-cut cryosections were deposited on glass slides and stored at −80° C. They were returned to room temperature 24 hours before the observations.

The sections were observed with a Bruker Multimode 8 microscope equipped with a Nanoscope V (Bruker) controller in tapping mode with a tip having a radius of curvature of approximately 10 nm (equivalent to the resolution of the assembly). The 512*512 pixel images were acquired at a scan rate of 1 Hz.

Three series of images of 3*3 $μm^2$ were acquired at different points, 100 μm and more apart, rather in the deep dermis. The condition for the zones to be observed was that they were relatively flat, without presence of significant asperities likely to damage the tip or the lever of the AFM.

The images were then processed with the Gwyddion software.

For confirmation, SAXS analysis was performed on the same samples.

The cryofixed samples were returned to room temperature 8 hours before the observations.

SAXS data collection:
Beamline ID02 (ESRF, France)
X-ray bean energy: 12.46 keV
Mode 7/8 multibunch
Beamsize on the sample: 150 (h)×100 (v) $μm^2$
Distance sample detector: 4 m
2D detector
Time exposure per pattern: 1 second
T=22° C., RH 40%
At least 20 diffraction patterns were collected per sample at various positions.

The data was processed with SAXSutilities software developed by ESRF. The diffraction profiles presented in this report were obtained by 360° angular integration of the 2D diffraction signal and subtraction of the average diffraction signal from the mica support.
Results Atomic Force Microscopy (AFM) showed a strong difference in the collagen organization in the dermis between that of a young donor and that of a mature donor. Indeed, the collagen fibers are very cohesive, well-organized and parallel in the young donor, while the mature donor had a much coarser and disorganized collagen fiber network.

Figure 3:
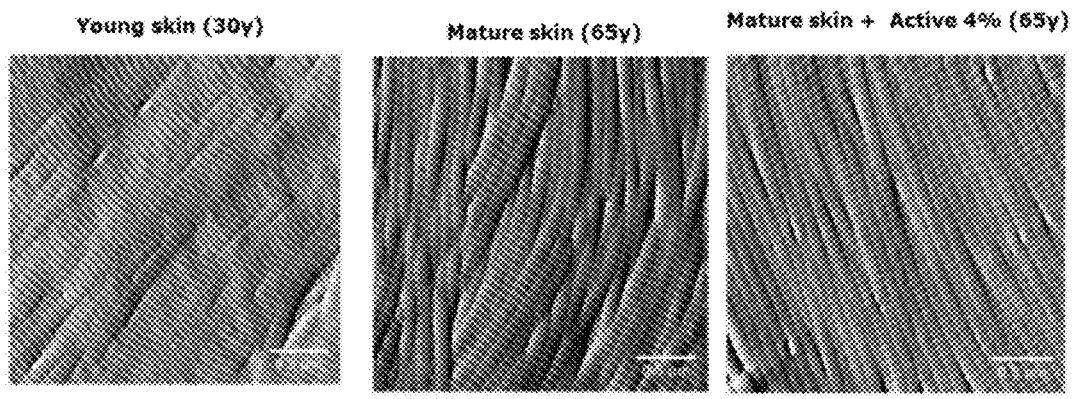

Treating mature skin with test composition 4 for 8 days led to an improved organization of the collagen fibers and increased cohesion between them (FIG. 3).

Using Small-angle X-ray scattering (SAXS) measurement, the quality of the collagen fiber organization can be correlated to the quantification data. Indeed, the more cohesive and well-organized a collagen fiber network is, the more intense and narrow is the peak observed in a SAXS measurement.

The SAXS profile confirmed large difference between young and mature donor: The collagen fibers of the mature donor are less organized and cohesive compared to those of the young donor. These results confirm that there is an age-related disorganization of collagen fibers.

Figure 4:
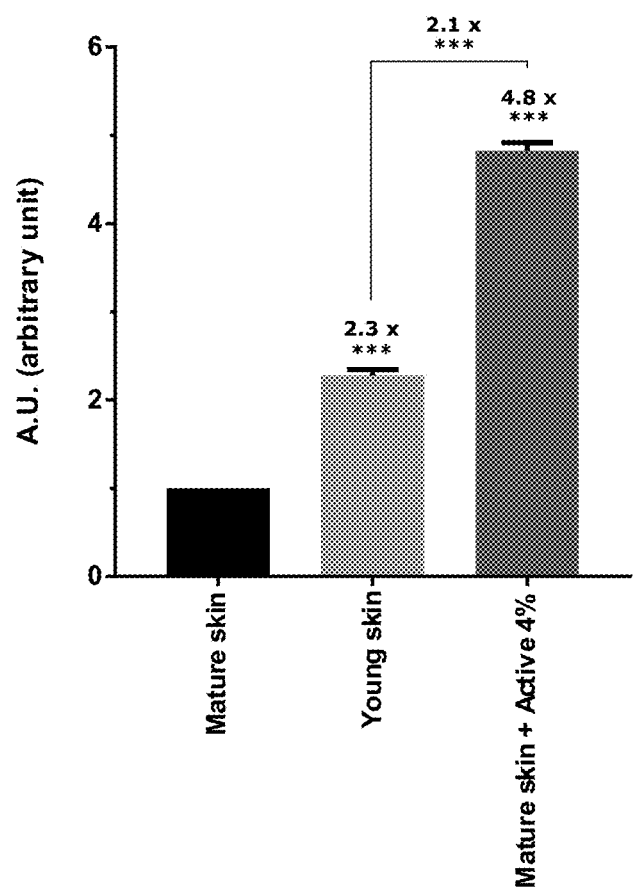

Treating mature skin explants with test composition 4 for 8 days lead to a strong improvement in SAXS profile, showing an even better organization than in young skin (FIG. 4).

Thus, SAXS measurement allowed confirming the observations obtained by the AFM study. Thus, the cosmetic active agent of the present invention has a strong impact on matrix restructuration by reorganizing collagen fibers: It improves collagen fibers' cohesion and organizes the dermis up to 4.8 times better than untreated observed in mature skin, and up to 2.1 times better than in untreated young skin.

EXAMPLE 9

Proteasome Activity

Skin Explants Treatment

NativeSkin® skin explants were used, a biopsy of human normal skin embedded in a solid and nourishing matrix. The epidermal surface was maintained in contact with air to allow topical application. The donor was a woman aged 59 years with Caucasian skin who had an abdominoplasty surgery.

For examples 6, 7, 8, and 9, test composition 4 was prepared by diluting the mixture of D-mannose-6-phosphate and D-mannose obtained according to example 1 at 4% (v/v) in PBS (Phosphate-buffered saline).

Test composition 4 was brought in contact with the NativeSkin® by topical application, which was removed and renewed every day during 7 days. The results were compared to the untreated skin explants.

Protein Extraction

At the time of analysis, samples were extracted and prepared for analysis using OxiProteomics' standard protein extraction methods adapted for skin explants samples. An internal positive control was generated and included in the analysis (C+).

Extracted proteins were quantified by the Bradford method and split into equal amounts for analyses.

Carbonyl Score Analysis

After extraction and solubilization, proteins in samples were quantified by the Bradford method using calibrated BSA as standard (Bradford M. Anal. Biochem., 72, 248 (1976). Absorbances were measured at 595 nm by triplicate and interpolated in the BSA standard curve for protein concentration determination.

After labeling carbonylated proteins with fluorescent probes, proteins were resolved onto 4-20% gradient SDS-PAGE. Proteins were fixed to the gel and carbonylated proteins were evidenced by fluorescence scanning. Total proteins were post-stained with SyproRuby.

Densitometric analysis of protein bands was performed using Image J analysis software (NIH, USA).

Density histograms and lane profile plots were obtained from each sample, both for carbonylated and total proteins. Carbonylated proteins signal was normalized by total proteins signal for each sample in order to obtain the carbonyl score.

$$\text{Carbonyl Score (sample } X) = \frac{\text{carbonylated prot.fluorescent signal (sample } X)}{\text{total prot.fluorescent signal (sample } X)}$$

Results

The results evidenced the ability of the active to protect proteins from oxidative damage in the three donors as observed by the reduction of carbonyl score. The carbonyl score is directly proportional to the proteasome activity. Thus, the cosmetic active agent of the present invention induces a significant improvement of proteasome activity of 20%.

EXAMPLE 10

Oxidized Protein Production

Treatments and UV Irradiation of Skin Explants

Skin explants from a 45 years old donor were stabilized with DMEM medium supplemented with antibiotics (penicillin 100 U/mL and streptomycin 100 µg/mL) and fetal calf serum 5% for 4 hours at 37° C./5% $CO_2$.

The explants were pre-treated for 24 hours, irradiated with UVA (8 $J/cm^2$) and UVB (0.2 $J/cm^2$), and treated again for 24 hours with active formulated, placebo or positive control. Three explants per condition were then frozen immediately in liquid nitrogen for preservation before cutting.

Immunostaining of Oxidized Proteins

Frozen skin explants were included in Tissue-Tek® before being cut with the cryostat. The sections had a thickness of 10 µM. The slides were stored at −20° C. before being dried and then fixed with acetone.

The sections were treated with DNPH (2,4-dinitrophenylhydrazine), which interacts with carbonyl groups on oxidized proteins.

Specific sites were blocked; primary antibody against DNP (dinitrophenyl) and secondary antibody coupled with alexa-type fluorochrome were used for the carbonylated proteins immunostaining. The nuclei were labeled with DAPI (Roche), a fluorescent marker specific for DNA. After each incubation, the sections were washed 3 times.

Fluorescence Quantification

Fluorescence quantification was performed using ImageJ software. Fluorescence of the total area of the section was measured on all images without DAPI. Shapiro Wilk test was performed, which allowed using student test to compare conditions.

Results

UV irradiation increases the amount of oxidized proteins in epidermis and dermis.

Treatment with placebo further promotes this raise: 35% more oxidized proteins compared to the irradiated control.

Figure 5:
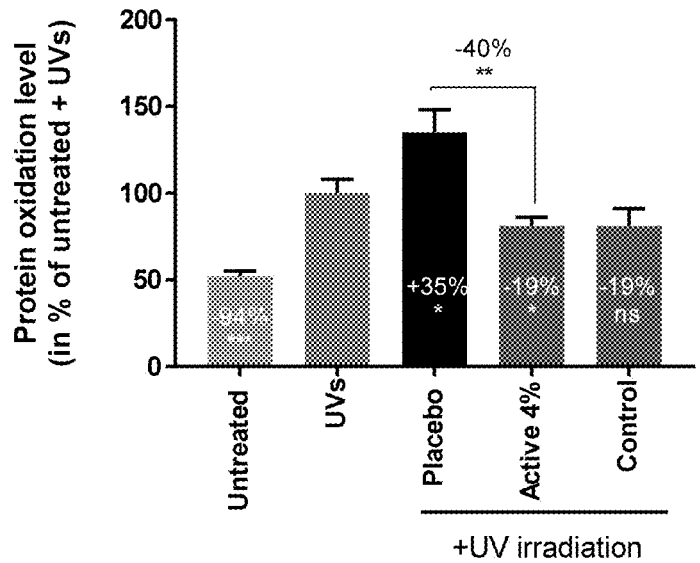

Interestingly, adding the active ingredient to the placebo not only prevented this increase, but even significantly reduced the amount of oxidized proteins by 19% compared to the irradiated control (UVs). Thus, the amount of oxidized proteins was reduced significantly by 40% in the presence of the active relative to placebo when the skin was irradiated with UVs. (FIG. 5)

These results evidenced that the cosmetic active agent of the present invention leads to a significant reduction of oxidized proteins.

EXAMPLE 11

Impact on Mitochondrial Mass

Materials and Method

The Mannose-6-Phosphate complex used in this example had the following composition: 1 g of an aqueous solution contained 0.11097 mmol mannose-6 phosphate (31.307 mg, molecular weight: 282.12 g/mol because of the monosodium form) and 0.07030 mmol mannose (12.663 mg, molecular weight: 180.16 g/mol).

Normal Human Dermal Fibroblasts were isolated from skin biopsy coming from a breast reduction surgery on a 17 years old woman. 10'000 cells per well were seeded in a black 96-wells plate with DMEM (Dulbecco's Modified Eagle's Medium, Gibco) supplemented with 10% FCS (Fetal Calf Serum, Biowest) and 1% antibiotics (Sigma Aldrich) and were cultured for 72 hours in an incubator at 37° C. in a humid atmosphere containing 5% $CO_2$. Cells were then rinsed two times with PBS (Phosphate Buffer Saline) before being incubated with FCS-free DMEM medium overnight in the same incubator. On the next day, the cells were treated with (i) mannose at 20 mM, (ii) mannose-6-phosphate at 20 mM or (iii) the above-mentioned Mannose-6-Phosphate complex at 20 mM (n=3) in the presence of insulin (100 nM). After 1 hour and 48 hours of treatment, MitoTracker™ Green FM (ThermoFisher) was added directly in each well for a final concentration of 200 nM and the plate was incubated in the dark in the incubator for 15 minutes. Cells were then rinsed off two times with PBS and each well was filled with 200 µl PBS. Fluorescence intensity of MitoTracker™ Green FM was measured with a microplate reader (Excitation wavelength: 488 nm/Emission wavelength: 525 nm).

Results

In this study, the mitochondrial mass in cells was determined using the fluorescence intensity emitted by MitoTracker™ Green FM.

Without being bound by theory, it is assumed that during cell starvation, there is a formation of a highly fused mitochondrial network, suggesting an increase of mitochondrial mass. Mitochondrial mass can also be increased if the mitophagy process is not activated to eliminate aged and altered mitochondria, which accumulate in the cells. It is believed that oxidative stress in cells results from this accumulation, which, on a long term, can lead to cellular death. Thus, mitophagy is an important phenomenon for cells' physiology, more especially the maintenance of mitophagy/mitochondrial biogenesis balance is essential to maintain cells in optimal conditions.

Figure 6:
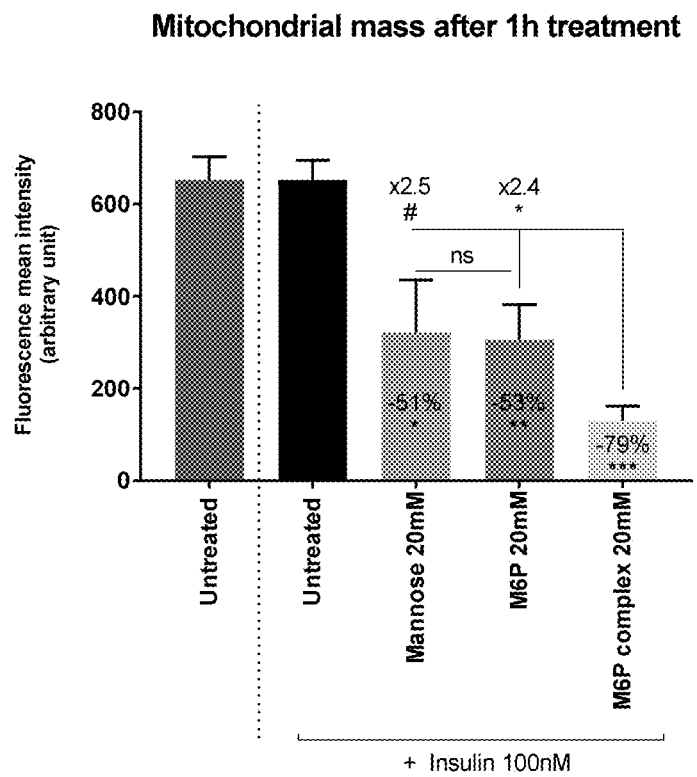
Figure 7:
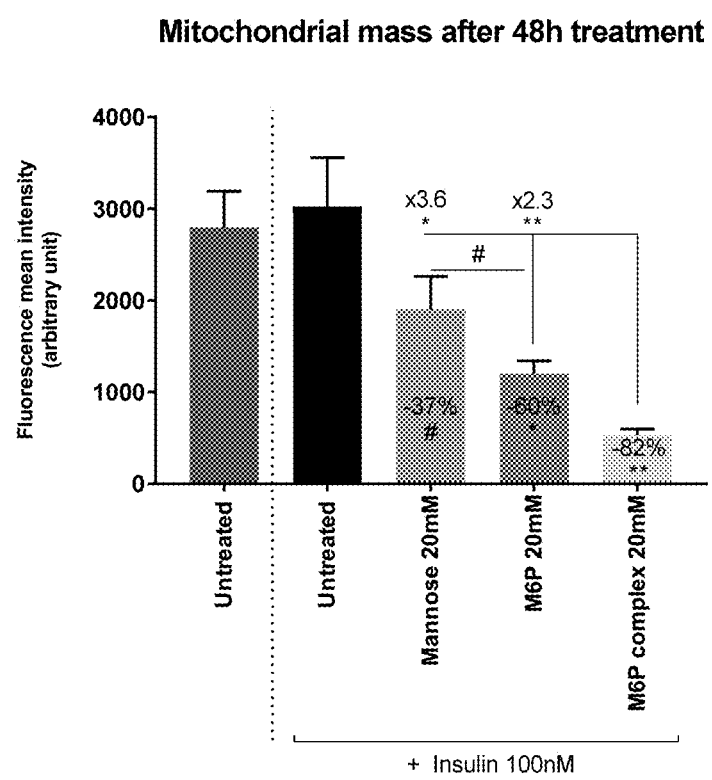

In this example, a significant decrease of MitoTracker™ Green FM specific signal after 1 hour treatment with (i) mannose, (ii) mannose-6-phosphate and (iii) the Mannose-6-Phosphate complex, each at 20 mM, by −51%, −53% and −79%, respectively, was observed (FIG. 6). After 48 hours of treatment, a significant decrease of the signal with (i) mannose, (ii) mannose-6-phosphate and (iii) the Mannose-6-Phosphate complex, each at 20 mM, by −37%, −60% and −82%, respectively, could also be observed (FIG. 7).

These results show a significant decrease of mitochondrial mass in cells, suggesting a reactivation of mitophagy with each active ingredient. Thus, oxidative stress in cells from aged and altered mitochondria is prevented and cells are maintained in optimal conditions.

More surprisingly, it was found that the Mannose-6-Phosphate complex was significantly more efficient: 2.5 times and 2.4 times after 1 hour, and 3.6 times and 2.3 times after 48 hours relative to mannose and mannose-6-phosphate alone, respectively, thus showing a synergistic biological effect on the reduction of mitochondrial mass of the Mannose-6-Phosphate complex.

EXAMPLE 12

Cosmetic Compositions Used for Clinical Studies

In the clinical studies described in examples 13 and 14 below, the following active and placebo, respectively, cosmetic compositions were used (INCI formulae; see also example 2):

Active: AQUA/WATER, CETYL ALCOHOL, GLYCERYL STEARATE, PEG-75 STEARATE, CETETH-20, STEARETH-20, ISODECYL NEOPENTANOATE, SODIUM MANNOSE-PHOSPHATE, MANNOSE, PHENOXYETHANOL, METHYL PARABEN, PROPYL PARABEN, ETHYL PARABEN, DIMETHICONE, FRAGRANCE, BENZYL SALLICYLATE, LINALOOL, D-LIMONENE Placebo: AQUA/WATER, CETYL ALCOHOL, GLYCERYL STEARATE, PEG-75 STEARATE, CETETH-20, STEARETH-20, ISODECYL NEOPENTANOATE, PHENOXYETHANOL, METHYL PARABEN, PROPYL PARABEN, ETHYL PARABEN, DIMETHICONE, FRAGRANCE, BENZYL SALLICYLATE, LINALOOL, D-LIMONENE

EXAMPLE 13

Anti-Aging Study on Facial Area (Clinical Study)

Panel Description

A double blind and placebo controlled clinical study was carried out on 22 volunteers (aged from 50 to 70 years, mean age: 59±4.9 years). Volunteers had to present crow's feet and nasolabial wrinkles and age spots on the face.

Volunteers applied twice a day a cosmetic cream on their face for 28 (D28) and 56 (D56) days: The active was applied on one hemiface and the placebo on the other hemiface (example 12). The collagen density was analyzed using SIAscope, and aging signs, such as wrinkles and age spots, by a VISIA analysis.

VISIA CR Analysis

Using Visia CR 2.3® from Canfield® imaging systems, digital photographs of the face were done at D28 and D56 with repositioning at D0. The control of the repositioning was done directly on data-processing screen using an overlay visualization of the images at each time of acquisition. The VISIA allows taking pictures with different types of illuminations and a very rapid capture of images. A series of photos taken under multi-spectral imaging and analysis allow capturing visual information affecting appearance of the skin.

Collagen Analysis by SIAscope

SIAscopy is a method of intra-cutaneous spectrophotometric analysis able to visualize the distribution of chromophores in the skin: melanin, hemoglobin and collagen up to 2 mm under the skin.

A SIAscope, portable scanning device connected to Siametrics software was used.

Placed in contact with the skin, the SIAscope illuminates the skin. Some of the light is reflected and scattered from the surface. The remainder is transmitted into the top layers of the skin. Varying fractions of the incoming light are absorbed by the melanin in the epidermis before entering the dermis where they are absorbed by the hemoglobin in the blood vessels. Scattering also occurs in the dermis when the light interacts with the collagen resulting in a portion of the light being remitted back to the surface. By interpreting the combination of wavelengths that are received back by the SIAscope, Siametrics is then able to produce SIAscans; these are generated by referring to inbuilt proprietary mathematical models of skin optics.

Results of Age Spots' Analysis

During aging, different types of spots are observed. The present study focuses on visible spots. The visible spots include all the small visible spots found in the skin. Visible spots are due to cell senescence and detoxification system disorder related to aging.

The number of visible spots was analyzed after 28 and 56 days of application. A significant 2.1-fold reduction of the number of visible spots relative to D0 and placebo was observed after 28 days (*p<0.05). The efficacy of the active was maintained after 56 days, with a significant decrease of the number of visible spots in comparison to the placebo (−1.9%, *p<0.05).

Considering the total spot area, the same tendency was observed, with a significant decrease of the total area of visible spots in comparison with D0 (−5.6%, *p<0.05) and placebo (−2.3%, *p<0.05) after 28 days.

Results of Collagen Density and Structure Measurements

The collagen density and organization were measured using SIAscope after D28 and D58 of application.

After 28 days, a significant improvement of collagen density relative to D0 and placebo was observed. In comparison with the placebo, the active lead to a significant increase of collagen organization by 3.8 times (p<0.05*).

After 56 days, similar results were obtained with a significant improvement of collagen density relative to D0 and placebo. The active improved the collagen organization 2.2 fold more than the placebo (p<0.05*).

These clinical results evidence the positive impact on collagen density and organization.

Results of Crow'S Feet Wrinkles Analysis

Focused on crow's feet wrinkles, it was found that the active caused a slight improvement compared the placebo after D28 of treatment (−4.6% vs. −3.0%). After 56 days of application, this effect was increased, as shown by the significant reduction of −11.5% compared to placebo (*p<0.05).

EXAMPLE 14

Anti-Aging Study on Neck Area (Clinical Study)

Panel Description

A double blind and placebo controlled clinical study was carried out on 39 volunteers (aged from 45 to 75 years, mean age: 56±6.2 years). Volunteers had to present wrinkles on neck area.

Volunteers applied twice a day a cosmetic cream containing 4% of the active or a placebo cream (example 12) on the entire face and neck for 28 (D28) and 56 (D56) days. The neck wrinkles were analyzed through the volume and the number of wrinkles using AEVA-HE® analysis.

Neck Wrinkle Analysis by AEVA-HE®

The AEVA-HE® system measures the effectiveness of a cosmetic product without skin contact. For this study, an AEVA-HE® system with 250 sensors was used in order to measure the depth, length and number of wrinkles. Based on a fringe projection unit using light associated with stereometry, the AEVA-HE® system offers high resolution 3D scanning. The volunteers were installed on VisioTOP-500 benches for accurate and stable positioning and re-positioning between the different measuring times.

Self-Assessment

In addition, a self-assessment questionnaire has given to each volunteer at D56. Volunteers were asked how they felt about the product they had used.

Results

Neck wrinkle volume was analyzed using 3D reconstruction from AEVA-HE®.

After 28 days of application, a significant reduction of −25.9% compared to D0 was observed with the active, while treatment with the placebo did not have a significant effect.

After 56 days of application, the effect was maintained with a significant reduction of wrinkle volume of −26.3% for the active. Again, the placebo did not exhibit a significant effect.

In addition, the neck wrinkle depth was also analyzed after application for 28 and 56 days.

After 28 days, a significant reduction of neck wrinkle depth by −11.4% was observed relative to D0, while the placebo only led to a reduction by −3.20% relative to D0.

After 56 days, the efficacy of the active was maintained with a significant decrease of −10.2% relative to D0, while the placebo did not exhibit a significant effect.

These results demonstrate that the cosmetic active ingredient of the present invention is able to significantly reduce neck wrinkles, both in terms of volume and depth.

The self-assessment analysis performed after 56 days of application revealed that:

84% of the volunteers were convinced by the efficacy of the active at the end of the study (60% for placebo), and 74% of the volunteers thought that their skin was firmer after the application of the active (45% for placebo).

The invention claimed is:

1. A cosmetic active agent comprising a mixture of mannose-6-phosphate and mannose, wherein the molar ratio of mannose-6-phosphate to mannose is from 3:1 to 0.3:1 and wherein the mannose-6-phosphate is comprised at a concentration of 30 to 220 mM.

2. The cosmetic active agent of claim 1, wherein the molar ratio of mannose-6-phosphate to mannose is from 2:1 to 1:1.

3. The cosmetic active agent of claim 2, wherein the molar ratio of mannose-6-phosphate to mannose is from 1.9:1 to 1.1:1.

4. The cosmetic active agent of claim 1, wherein the cosmetic active agent at-least-essentially consists of the mixture of mannose-6-phosphate and mannose.

5. The cosmetic active agent of claim 1 which comprises 0.5 to 5.0 wt % of mannose.

6. The cosmetic active agent of claim 1, further comprising glycerol and/or sodium phosphate.

7. The cosmetic active agent of claim 1, comprising:

| | |
|---|---|
| 2.0 to 4.0 wt % | mannose-6-phosphate sodium salt |
| 0.8 to 3.0 wt % | mannose |
| up to 0.2 wt % | sodium phosphate |
| 50 wt % | glycerol |
| qsp 100 wt % | water. |

8. A cosmetic composition comprising the cosmetic active agent of claim 1 and a cosmetically acceptable excipient.

9. An anti-aging skin care composition comprising the cosmetic composition of claim 8.

10. A method of reducing the signs of aging in skin, comprising the step of applying the cosmetic active agent of claim 1 to the skin.

11. The method of claim 10, wherein wrinkles are reduced.

12. The method of claim 10, wherein age spots are reduced.

13. The method of claim 10, wherein collagen fibers are structured.

14. The method of claim 10, wherein the skin is facial skin.

15. The cosmetic active agent of claim 1 which comprises mannose-6-phosphate in a concentration of 60 to 170 mM.

16. The cosmetic active agent of claim 1 which comprises 0.8 to 3.0 wt % of mannose.

\* \* \* \* \*